United States Patent [19]
Rao et al.

[11] Patent Number: 5,871,485
[45] Date of Patent: Feb. 16, 1999

[54] DEVICE FOR INTERNAL FIXATION OF FEMORAL NECK FRACTURES

[76] Inventors: G.V. Subba Rao, 806 East Mary La.; Anil K. Goli, 153 East Halt Dr., both of Terre Haute, Ind. 47802

[21] Appl. No.: 40,709

[22] Filed: Mar. 18, 1998

[51] Int. Cl.⁶ .................................................. A61B 17/76
[52] U.S. Cl. ............................................................. 606/65
[58] Field of Search ............................ 606/65, 66, 67, 606/68, 73, 60

[56] References Cited

U.S. PATENT DOCUMENTS

| | | | |
|---|---|---|---|
| 2,801,631 | 8/1954 | Charnley | 606/65 |
| 3,256,877 | 6/1966 | Haboush | 606/67 |
| 3,554,193 | 1/1971 | Konstantinou | 606/65 |
| 5,041,116 | 8/1991 | Wilson | 606/65 |
| 5,127,914 | 7/1992 | Calderale et al. | 606/65 |
| 5,562,667 | 10/1996 | Shuler et al. | 606/64 |

*Primary Examiner*—Guy V. Tucker
*Attorney, Agent, or Firm*—H. John Barnett

[57] ABSTRACT

An internal fixation device used in surgical procedures to the internal fixation of femoral hip fractures, especially prevalent in elderly persons suffering from osteoporosis. This device includes a femoral shaft side plate, an internally threaded sleeve pivotally mounted on said side plate, an elongated screw member insertable in the sleeve to fasten the sleeve in the femoral head, and wedge-shaped washer means for fixing the pivot angle between the sleeve and the femoral side plate at the natural angle between the axis of the femoral neck the femoral shaft of the hip being treated.

5 Claims, 2 Drawing Sheets

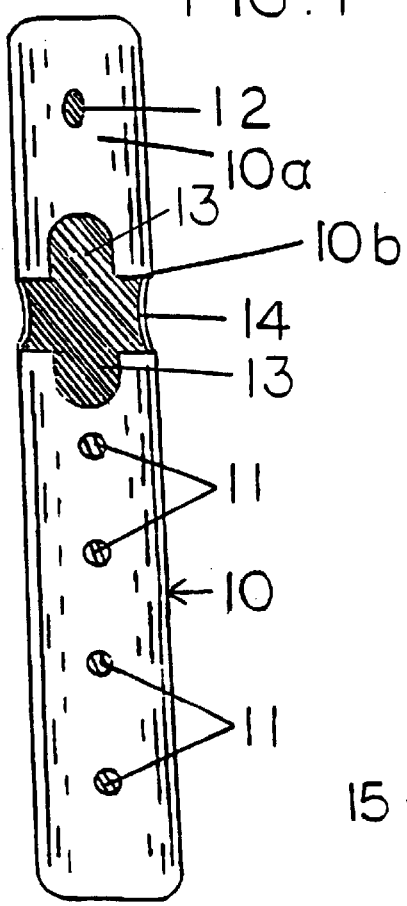
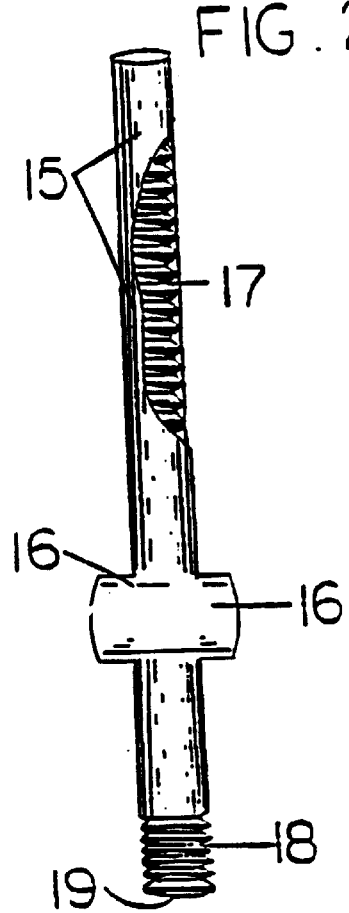
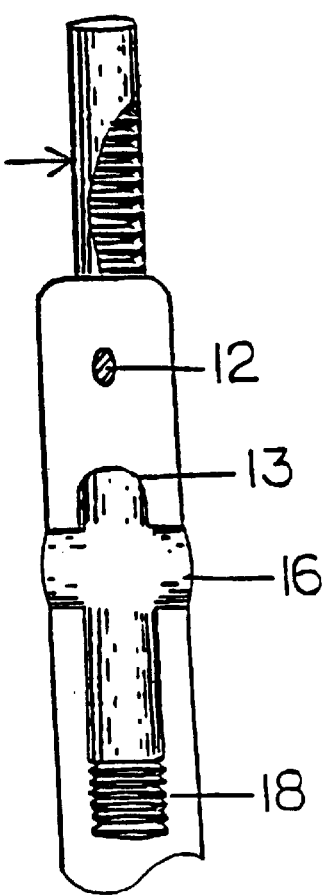
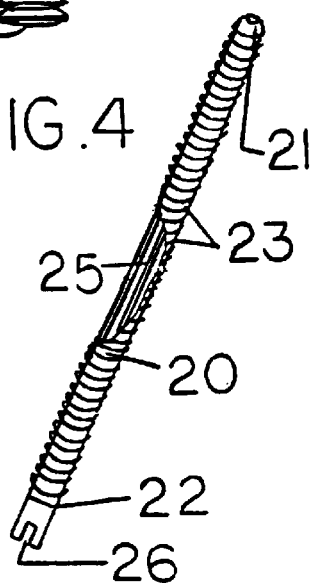

DEVICE FOR INTERNAL FIXATION OF FEMORAL NECK FRACTURES

BACKGROUND OF THE INVENTION

1. Field of the Invention

This invention relates to fixation devices used in surgical procedures to the internal fixation of femoral neck fractures. Femoral neck fractures are the most common, and they are especially prevalent in elderly persons suffering from osteoporosis. Many internal fixation devices have been proposed for treating femoral neck fractures, but until now, none of these have included a simple means to make such devices universally applicable to all patients, even though they have a wide variation in their respective femoral neck angles.

2. Description of the Related Art

The following patents are related to fixation devices for the internal fixation of femoral neck fractures:

| Patent Number | Inventor | Date |
| --- | --- | --- |
| 2,441,765 | Hopkins | 1948 |
| 2,500.993 | Mason | 1948 |
| 2,801,631 | Charnley | 1957 |
| 3,256,877 | Haboush | 1966 |
| 3,554,193 | Konstantinou | 1971 |
| 5,127,914 | Calderale, et al | 1992 |
| 5,462,547 | Weigum | 1995. |

Hopkins '765 is directed to a surgical device for internal fixation of intertrochanteric fractures of the femur which provides an adjustable angle between the fixation nail and the extension arm to hold the nail in position. The hemispherical end of the fixation nail fits into a socket on the end of the extension arm, the outer surface of which is provided with cooperating serrations or teeth which mesh with matching teeth of a partially spherical washer to secure the nail and the washer at a predetermined angle when a cap screw is tightened into the nail over the washer. Even a small loosening the cap screw which can happen during the fixation period can permit shifting between the nail and the extension arm. Also, the Hopkins device is complex, and relatively expensive to manufacture.

Charnley '631 shows a later device which has a fixed angle between an extension arm and a tubular part which surrounds a fixation screw. A number of fixed angle devices having different angles must be available to the surgeon during the operation so that the optimum angle selection can be made. If the fixation device selected is incorrect, it cannot be adjusted in situ, but must be completely removed, with very serious consequences to the patient.

Haboush '877 is a later development which is somewhat similar to Hopkins in that Haboush also interconnects his fixation nail and plate (extension arm) by means of a ratchet joint (serrations or teeth). Haboush's joint is fastened from the side by screws. Both screws must remained securely fastened during the healing process for this device to work. As with Hopkins, even a slight loosening of either screw could permit a shifting of the angle between the fixation nail and plate. The Haboush device is also complex, and, therefore, expensive to manufacture.

Calderale, et al '914 describe an elongated plate which is secured to the shaft of the femur, and which has a angle joint in its upper end. This plate is disposed at the upper end of the femur just below the greater trochanter, and opposite the femoral head. Adjustable elements 15 receive a pair of screws 8, which extend through the fractured femoral neck and rigidly anchor the shaft of the femur to the femoral head. The elements 15 are spherical, and fit into spherical seats 19. A plate 21 holds the elements in place by tightening connecting member 22. The device is complex, and, therefore, expensive to manufacture. Only slight loosening of member 22 would allow the angle to shift during the healing period.

Weigum '547 is directed to a similar device which comprises a sleeve strap and a trochanter stabilization plate. The sleeve strap includes an integral sleeve which has a fixed angle. The sleeve extends into the trochanter towards the femoral head, and provides a passage for a bone screw. The Weigum apparatus is expensive to use, because a plurality of sleeve straps must be provided with every unit shipped to be sure that one is available having the correct angle for the sleeve. A wide variation between femoral neck angles exists in different patients. As with Charnley, selecting the wrong angle can have very serious consequences because the device cannot be adjusted in situ, but must be removed and replaced if the selected sleeve strap does not have the correct angle.

None of the above patents show a combination of a femoral plate which provides a pivotal mount for an adjustable angle sleeve, and a pivotable sleeve for insertion into a femoral neck at an optimum angle. The sleeve is then held at that angle by means of a wedge-shaped washer and retaining nut, which are tightly fit onto the outer end of the sleeve.

SUMMARY OF THE INVENTION

This invention provides a versatile internal fixation device for stabilizing femoral neck fractures. A side plate which attaches to the femoral shaft is provided with pivot means at its upper end to pivotally receive the outer end of a sleeve which is inserted into the central portion of the femoral neck at an angle to the femur shaft corresponding the natural angle of the patient's femur before the fracture.

The angle between the sleeve and the side plate is then fixed by selecting and installing a wedge-shaped washer on the sleeve to hold the sleeve at the desired angle. The washer is held in place at the correct angle by a retaining nut which urges the washer against a shoulder on the side plate.

The subject invention is more economical than similar prior art devices, because only a relatively inexpensive, wedge-shaped washer is needed to hold the sleeve and the femoral shaft side plate at the correct angle. For each surgical procedure to repair a femoral neck fracture, it is only necessary to have a plurality of wedge washers available in a range of angles in order to select and install the correct angle wedge washer in the internal fixation device of the invention.

BRIEF DESCRIPTION OF THE DRAWING

FIG. 1 of the drawings is a plan view of a femoral shaft side plate for stabilizing a femoral neck fracture;

FIG. 2 is a plan view of an elongated sleeve, broken away in part to show the internal threads, and showing laterally disposed pivot protuberances;

FIG. 3 is a plan view of the upper end of the side plate with the elongated sleeve pivotally disposed therein;

FIG. 4 is a broken away side view of the inner screw member;

As shown in FIG. 1, an elongated side plate 10 is provided with a plurality of openings 11 for receiving femoral shaft anchor screws 36, best seen in FIG. 6. Side plate 10 has an uppermost angular opening 12 for receiving a trochanteric anchor screw (not shown). Between the angular opening 12 and the uppermost opening 11, is an oblong opening 13 having a pair of pivot seats 14.

Figure 6:
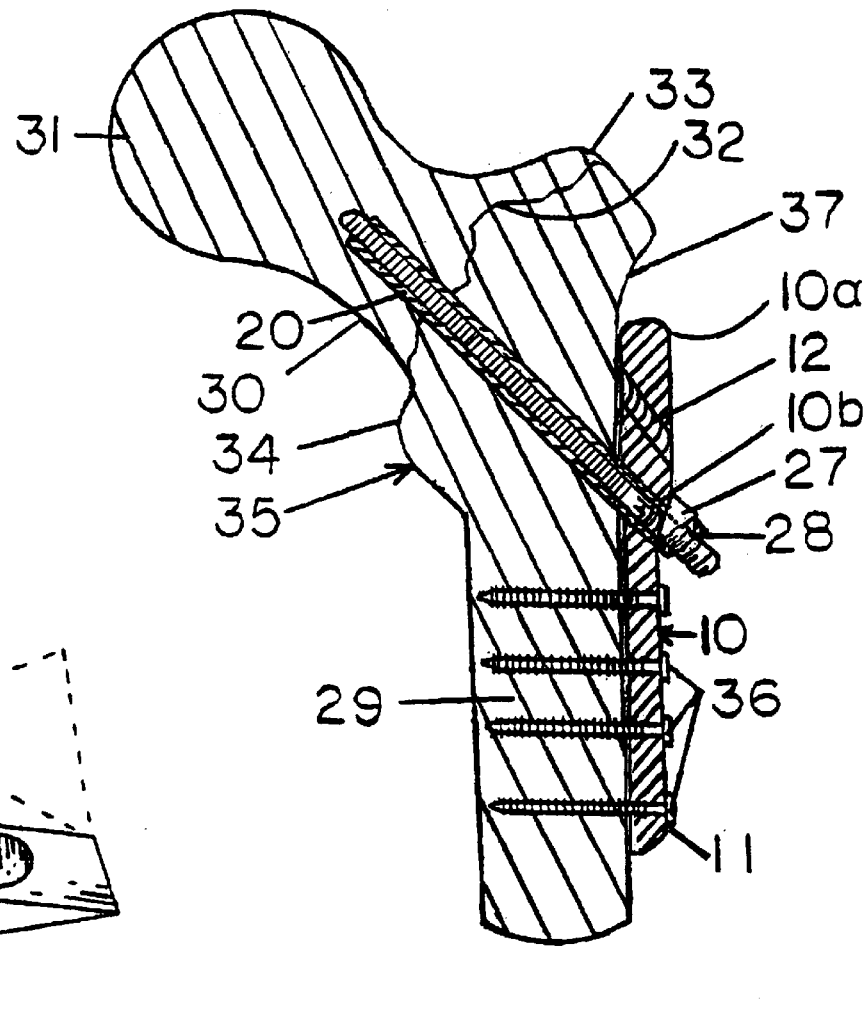
FIG. 6 is a front, vertical sectional view of the fixation device in place in a fractured femur, with the lower femur not shown.

As can be seen in FIGS. 6, upper ends 10a of the side plate 10 is thicker, and includes shoulder 10b. The upper portion of oval opening 13 extends through the mid-portion of shoulder 10b, as best seen in FIG. 1, to provide clearance for a wide range of pivot angles for an elongated sleeve 15.

FIG. 2 shows the elongated sleeve 15 which is provided with a pair of protuberances 16, which are adapted to be disposed in pivot seats 14, as seen in FIG. 3. The elongated sleeve 15 has internal threads 17 throughout its length, and external threads 18 at outer end 19, which is closest to the protuberances 16.

FIG. 3 shows the elongated sleeve 15 extending through the oblong opening 13 with the protuberances 16 pivotally seated in the pivot seats 14. The sleeve 15 can be pivoted from an angle of about 125 degrees to about 150 degrees relative to the axis of the side plate 10.

An inner screw member 20 having an inner end 21, and outer end 22 is shown in FIG. 4. Screw member 20 has complementary threads 23, and is adapted to be threadably received in the sleeve 15 with the end 21 extending out end 24 of the sleeve 15. If necessary, screw member 20 can be removed from the sleeve 15, even during the surgical procedure, and replaced with a shorter or longer screw member 20 as required. A screwdriver slot 26 is provided on the outer end 22 of the screw member 20 to turn screw member 20 in the sleeve 15.

If it becomes necessary to make an adjustment in the screw member 20, or to replace it after the initial surgical procedure, it is only necessary for the surgeon to make a small incision to access the end of the sleeve 15 so that the screw member can be removed and replaced, or adjusted in its position in the sleeve 15. Such adjustments are not possible with prior internal fixation devices. The patient must go through another major surgical procedure, and consequent possible trauma if one of the earlier devices requires adjustment.

The screw member 20 includes a cannula 25, best seen in FIG. 4, which extends axially throughout the length of the screw member 20. The cannula 25 provides access for a guide pin which is used during the surgical procedure to assist in precision placement of the internal fixation device to facilitate healing of the femoral fracture.

Figure 5:
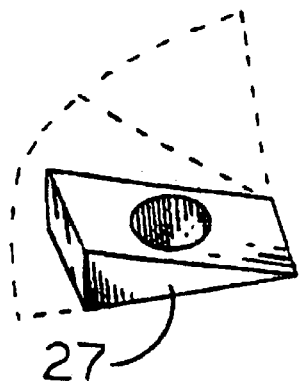
FIG. 5 is a perspective view of the wedge washer with a range of angle slopes shown in phantom.

A wedge-shaped washer 27 is shown in FIG. 5. Washer 27 fits over end 19 of the sleeve 15 to fix the angle between the sleeve 15 and the shoulder 10b of the side plate 10. A retaining nut 28 is threadably received on the end 19 of the sleeve 15 to firmly set the wedge-shaped washer 27 in position between the sleeve 15 and the shoulder 10b of the side plate 10, corresponding to the natural angle between the femoral shaft 29 and neck 30 of femoral head 31, as best seen in FIG. 6.

FIG. 6 shows the fixation device of the invention assembled to stabilize a femoral neck fracture 32 extending between greater trochanter 33 and lesser trochanter 34 of a human femur 35. As can be seen in FIG. 6, side plate 10 is held in place by a plurality of threaded screws 36 which extend transversely through opening 11 into femoral shaft 29. An optional threaded screw 36 (not shown) may extend diagonally into upper end 37 of the femoral shaft 29 through diagonal opening 12, if further stabilization is required for side plate 10.

As best seen by the phantom lines in FIG. 5, the wedge-shaped washer 27 is made in any number of wedge angles. These washers are made available to the surgeon during the surgical procedure, so that the correct wedge angle may be selected to fit the natural angle between the femoral neck and the femoral shaft This invention provides an improved internal fixation device for femoral neck fractures. The pivotal sleeve may be inserted into the femoral neck at the correct natural angle, the side plate fastened to the femoral shaft, and the inner screw member 20 may be screwed up through the sleeve 15 and into the femoral head to fix the fracture in correct position for healing. Finally, a wedge-shaped washer is selected which will hold the fixation device at the correct natural angle. The correct washer is assembled on the outer end of the sleeve and held firmly in place by the retaining nut.

The internal fixation device components may be fabricated from a number of materials suitable for human implantation. Such materials include stainless steel, titanium and titanium alloys, vitallium, chromium and chromium alloys, and other specialized materials and combinations thereof. The important properties of the selected materials is that they remain inert, be impervious to the internal body environ, and be sufficiently strong to provide effective support during the healing process.

What is claimed is:

1. An improved hip fracture internal fixation device comprising:

a femoral shaft support plate having an upper end and a lower end, said plate being adapted to be attached outwardly to the upper end of the shaft of a human femur having a hip fracture, first pivot means formed in said femoral shaft support plate near the upper end thereof, an internally threaded tubular sleeve having an upper end and a lower, externally threaded end, said sleeve having complementary pivot means adjacent the lower end thereof to pivotally engage said first pivot means, said sleeve being adapted to be inserted into a surgically drilled passage extending centrally and generally coaxially through the femoral neck at the natural angle thereof from the femoral shaft, and through said hip fracture to fix it in a natural healing position, an elongated screw member having an upper end and a lower end, adapted to be threadably received in said tubular sleeve so that the upper end of said screw member extends out the upper end of said sleeve into the body of the femoral head to firmly fix the hip fracture in aligned position, and angle fixation means adapted to be received on the lower end of said sleeve, said angle fixation means being adapted to engage the upper end of the shaft support plate to hold the angle between the support plate and said sleeve at the natural angle between the axis of the femoral neck and the axis of the human femur being treated.

2. The internal fixation device of claim 1, in which the first pivot means comprises a pair of recesses formed in the upper end of the femoral shaft support plate, and the complementary pivot means comprises a pair of protuberances formed on opposite sides of the tubular sleeve, said protuberances each adapted to be pivotally received in a corresponding recess in said femoral support plate.

3. The fixation device of claim 2, including an oval opening extending through said femoral support plate between said recesses, said tubular sleeve normally extending through said oval opening when it is pivotally assembled on said support plate.

4. The internal fixation device of claim 1, in which the angle fixation means comprises:

a wedge-shaped washer adapted to be received on the lower end of the tubular sleeve, said washer being adapted to engage the upper end of the femoral shaft support plate to hold the support plate and said sleeve at the natural angle between the axis of the femoral neck and the axis of the human femur being treated; and a retaining nut threadably received on the lower end of said tubular sleeve for firmly holding the angle fixation device at said natural angle.

5. The internal fixation device of claim 1, in which the support plate, tubular sleeve, screw member, and angle fixation means are fabricated from a material selected from stainless steel, titanium alloys, vitallium, nylon and other materials suitable for human implantation, and combinations thereof.

* * * * *